United States Patent [19]
Burdett, Jr.

[11] Patent Number: 6,093,876
[45] Date of Patent: Jul. 25, 2000

[54] COTTON PLANT NAMED 926 B PIMA

[75] Inventor: Lawrence P. Burdett, Jr., Casa Grande, Ariz.

[73] Assignee: Delta and Pine Land Company, Scott, Miss.

[21] Appl. No.: 09/348,018

[22] Filed: Jul. 6, 1999

Related U.S. Application Data

[62] Division of application No. 09/116,571, Jul. 16, 1998, abandoned.

[51] Int. Cl.⁷ .............................. A01H 5/00; A01H 5/10; A01H 4/00; A01H 1/04; C12N 5/04
[52] U.S. Cl. .......................... 800/314; 800/298; 800/260; 435/427; 435/430
[58] Field of Search .................................. 800/314, 298, 800/260, 269; 435/427, 430

[56] References Cited

U.S. PATENT DOCUMENTS 5,695,999  12/1997  Rangan et al. ........................... 435/427

OTHER PUBLICATIONS

Bi et al. Biotechno., Agron., Soc. Environ. vol. 1, pp. 142–150, 1997.
Ikramov et al. Dokl. Akad Nauk Resp. Uzb vol. 4, pp. 59–61, 1995.
Nielsen et al. Chapet 13, Breeding Plants Resistant to Insects. Maxwell et al. Eds. John Wiley and Sons, New York, pp. 285–288, 1980.
Jensen, Neal F., *Plant Breeding Methodology*, pp. 49–61 (date unknown).
Allard, R.W., *Principles of Plant Breeding*, Chapters 14 & 34, pp. 150–165 and 434–443 (1960).
Turcotte, E.L., and Carl V. Feaster, "Effectsof $R_1$, A Gene for Red Plant Color, on American Pima Cotton," *Crop Science*, pp. 875–876 (Nov.–Dec., 1975).
Turcotte, E.L., and Carl V. Feaster, "Registration of Five American Pima Cotton Germplasm Lines," *Crop Science*, p. 206 (Jan.–Feb., 1986).

*Primary Examiner*—Gary Benzion
*Assistant Examiner*—Melissa L. Kimball
*Attorney, Agent, or Firm*—Rothwell, Figg, Ernst & Kurtz

[57] ABSTRACT

The present invention relates to a method for rapidly introducing genes into germplasm which involves the use of crossing, backcrossing, intense selection and agronomic trait selection. More specifically, the method comprises the steps of: (a) crossing two parents of two different species, one of the parents (the donor parent) contains the gene of interest; (b) backcrossing the resultant progeny with the parent not containing the gene of interest (recurrent parent) for two to four backcrosses; (c) performing intense selection on a segregating generation of the progeny from the backcrossing step; and (d) selecting final germplasm on the basis of desired agronomic traits. The present invention further relates to two new and distinctive high yielding Pima Bt (*Bacillus thuringiensis*) Bollgard® cotton cultivars, designated 926 B Pima and 930 B Pima, which have been prepared in accordance with the method of the present invention.

15 Claims, No Drawings

COTTON PLANT NAMED 926 B PIMA

This application is a divisional of U.S. patent application Ser. No. 09/116,571 filed Jul. 16, 1998 now abandoned.

BACKGROUND OF THE INVENTION

The present invention relates to a method for rapidly introducing genes into germplasm which involves the use of crossing, backcrossing, intense selection and agronomic trait selection. More specifically, the method comprises the steps of: (a) crossing two parents of two different species, one of the parents (the donor parent) contains the gene of interest; (b) backcrossing the resultant progeny with the parent not containing the gene of interest (recurrent parent) for two to four backcrosses; (c) performing intense selection on a segregating generation of the progeny from the backcrossing step; and (d) selecting final germplasm on the basis of desired agronomic traits. The present invention further relates to two new and distinctive high yielding Pima Bt (*Bacillus thuringiensis*) cotton cultivars, designated 926 B Pima and 930 B Pima, which have been prepared in accordance with the method of the present invention.

The publications and other materials used herein to illuminate the background of the invention, and in particular, cases to provide additional details respecting the practice, are incorporated by reference, and for convenience are referenced in the following text by author and date and are listed alphabetically by author in the appended bibliography.

There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety an improved combination of desirable traits from the parental germplasm.

Pureline cultivars, such as generally used in cotton and many other crops, are commonly bred by hybridization of two or more parents followed by selection. The complexity of inheritance, the breeding objectives and the available resources influence the breeding method. Pedigree breeding, recurrent selection breeding and backcross breeding are breeding methods commonly used in self pollinated crops such as cotton. These methods refer to the manner in which breeding pools or populations are made in order to combine desirable traits from two or more cultivars or various broad-based sources. The procedures commonly used for selection of desirable individuals or populations of individuals are called mass selection, plant-to-row selection and single seed descent or modified single seed descent. One, or a combination of these selection methods, can be used in the development of a cultivar from a breeding population. Descriptions of breeding methods that are commonly used for different traits and crops can be found in one of several reference books (e.g., Allard, 1960; Welsh, 1981; Fehr, 1987; Mayo, 1987).

Pedigree breeding is primarily used to combine favorable genes into a totally new cultivar that is different in many traits than either parent used in the original cross. It is commonly used for the improvement of self-pollinating crops. Two parents which possess favorable, complementary traits are crossed to produce an $F_1$ (filial generation 1). An $F_2$ population is produced by natural selfing of plants or by physically selfing the plants. Selection of desirable individual plants may begin as early as the $F_2$ generation wherein maximum gene segregation occurs. Individual plant selection can occur for one or more generations. Successively, seed from each selected plant can be planted in individual, identified rows or hills, known as progeny rows or progeny hills, to evaluate the line and to increase the seed quantity, or, to further select individual plants. Once a progeny row or progeny hill is selected as having desirable traits it becomes what is known as a breeding line that is specifically identifiable from other breeding lines that were derived from the same original population. At an advanced generation (i.e., $F_5$ or higher) seed of individual lines are evaluated in replicated testing. At an advanced stage the best lines or a mixture of phenotypically similar lines from the same original cross are tested for potential release as new cultivars.

The single seed descent procedure in the strict sense refers to planting a segregating population, harvesting one seed from every plant, and combining these seeds into a bulk which is planted the next generation. When the population has been advanced to the desired level of inbreeding, the plants from which lines are derived will each trace to different $F_2$ individuals. Primary advantages of the seed descent procedures are to delay selection until a high level of homozygosity (e.g., lack of gene segregation) is achieved in individual plants, and to move through these early generations quickly, usually through using winter nurseries.

The modified single seed descent procedures involve harvesting multiple seed (i.e., a single lock or a simple boll) from each plant in a population and combining them to form a bulk. Part of the bulk is used to plant the next generation and part is put in reserve. This procedure has been used to save labor at harvest and to maintain adequate seed quantities of the population.

Backcrossing is the preferred method of transferring one or more simply inherited genes from one variety (the donor parent) to a second variety (the recurrent parent). The $F_1$ is continually crossed with the recurrent parent until the recurrent parent is recovered. Backcrossing is simple, requires small plant populations and generates results quickly. The accumulation of genes from the recurrent parent increases at a rate of 50% with each backcross.

The number of backcrosses required to recover the recurrent parent increases as the genetic distance between the donor and recurrent parent diverge. Backcrosses involving interspecific parents represent extreme genetic distance. Deleterious genetic interactions and even problems at the chromosome level are common. Numerous backcrosses are necessary to recover the recurrent parent.

The recovery of the recurrent parent is based on the probability of moving closer to that parent by 50% with each backcross, randomly. When deleterious genetic interactions occur, even with 99.99% of the genome of the recurrent parent reclaimed, it may not be sufficient. A gene or many genes responsible for the deleterious genetic interactions may be still present in the 0.01% of the donor parent DNA. Insignificant ratios of recurrent parent/donor parent DNA can have significant consequences in plant genomes.

Selection for desirable traits can occur at any segregating generation ($F_2$ and above). Selection pressure is exerted on a population by growing the population in an environment where the desired trait is maximally expressed and the individuals or lines possessing the trait can be identified. For instance, selection can occur for disease resistance when the plants or lines are grown in natural or artificially-induced disease environments, and the breeder selects only those individuals having little or no disease and are thus assumed to be resistant.

Promising advanced breeding lines are thoroughly tested and compared to popular cultivars in environments representative of the commercial target area(s) for three or more years. The best lines having superiority over the popular cultivars are candidates to become new commercial cultivars. Those lines still deficient in a few traits are discarded or utilized as parents to produce new populations for further selection.

These processes, which lead to the final step of marketing and distribution, usually take from seven to twelve years from the time the first cross is made. Therefore, development of new cultivars is a time-consuming process that requires precise forward planning, efficient use of resources, and a minimum of changes in direction.

A most difficult task is the identification of individuals that are genetically superior because, for most traits the true genotypic value is masked by other confounding plant traits or environmental factors. One method of identifying a superior plant is to observe its performance relative to other experimental lines and widely grown standard cultivars. For many traits a single observation is inconclusive, and replicated observations over time and space are required to provide a good estimate of a line's genetic worth.

The two cotton species commercially grown in the United States are Gossypium hirsutum, commonly known as short staple or upland cotton and Gossypium barbadense, commonly known as extra long staple (ELS) or, in the United States, as Pima cotton. Upland cotton fiber is used in a wide array of coarser spin count products. Pima cotton is used in finer spin count yarns (50–80) which are primarily used in more expensive garments. Other properties of Pima cotton are critical because of fiber end use.

Cotton is an important and valuable field crop. Thus, a continuing goal of plant breeders is to develop stable, high yielding cotton cultivars that are agronomically sound. The reasons for this goal are obviously to maximize the amount and quality of the fiber produced on the land used and to supply fiber, oil and food for animals and humans. To accomplish this goal, the cotton breeder must select and develop plants that have the traits that result in superior cultivars.

G. barbadense is a cultivated species of cotton denoted by the genome (AD)2. Peru is the proximate area considered to be the center of origin for the species. G. barbadense varieties grown in the United States are commonly referred to as "American Pima", Pima or ELS cottons. The terms "American Pima", Pima and ELS are elucidated in the Definitions listed below.

It is often desired to introduce traits from one cotton species into the other. Such interspecific crosses are generally hard to work with because the chromosomes of the distinct species involved do not pair well in the progeny. The consequence is a large number of progeny that are very poor relative to either parent post $F_1$ generation. Interspecific crosses between upland and Pima species, where selection toward the Pima parent is desired, is further complicated by the fact that Pima fiber traits are held to very high standards.

The goal of a commercial cotton breeding program is to develop new, unique and superior cotton cultivars. In cotton, the important traits include higher fiber (lint) yield, earlier maturity, improved fiber quality, resistance to diseases and insects, tolerance to drought and heat, and improved agronomic traits. The breeder initially selects and crosses two or more parental lines, followed by generation advancement and selection, thus producing many new genetic combinations. The breeder can theoretically generate billions of different genetic combinations via this procedure. The breeder has no direct control over which genetic combinations will arise in the limited population size which is grown. Therefore, two breeders will never develop the same line having the same traits.

Each year, the plant breeder selects the germplasm to advance to the next generation. This germplasm is grown under unique and different geographical, climatic and soil conditions, and further selections are then made, during and at the end of the growing season. The lines which are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he develops, except possibly in a very gross and general fashion. The same breeder cannot produce, with any reasonable likelihood, the same cultivar twice by using the exact same original parents and the same selection techniques. This unpredictability results in the expenditure of large amounts of research moneys to develop superior new cotton cultivars.

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, and the grower, processor and consumer; for special advertising and marketing and commercial production practices, and new product utilization. The testing preceding the release of a new cultivar should take into consideration research and development costs as well as technical superiority of the final cultivar. For seed-propagated cultivars, it must be feasible to produce seed easily and economically.

The development of new cotton cultivars requires the evaluation and selection of parents and the crossing of these parents. The lack of predictable success of a given cross requires that a breeder, in any given year, make several crosses with the same or different breeding objectives.

The cotton flower is monecious in that the male and female structures are in the same flower. The crossed or hybrid seed is produced by manual crosses between selected parents. Floral buds of the parent that is to be the female are emasculated prior to the opening of the flower by manual removal of the male anthers. At flowering, the pollen from flowers of the parent plants designated as male, are manually placed on the stigma of the previous emasculated flower. Seed developed from the cross is known as first generation ($F_1$) hybrid seed. Planting of this seed produces $F_1$ hybrid plants of which half their genetic component is from the female parent and half from the male parent. Segregation of genes begins at meiosis thus producing second generation ($F_2$) seed. Assuming multiple genetic differences between the original parents, each $F_2$ seed has a unique combination of genes.

There is a need in the art to increase the efficiency of breeding new cultivars having agronomically improved traits, especially new cultivars derived from interspecies. There is also a need in the art to develop new cultivars of Pima cotton which contain the Bt gene. The present invention describes a method for rapidly introducing genes into germplasm, such as the Bt gene (Bollgard®) into Pima cotton, and thus satisfies these needs.

SUMMARY OF THE INVENTION

The present invention relates to a method for rapidly introducing genes into germplasm which involves the use of crossing, backcrossing, intense selection and agronomic trait selection. More specifically, the method comprises the steps of: (a) crossing two parents of two different species, one of the parents (the donor parent) contains the gene of interest; (b) backcrossing the resultant progeny with the parent not containing the gene of interest (recurrent parent) for two to four backcrosses; (c) performing intense selection on a segregating generation of the progeny from the backcrossing step; and (d) selecting final germplasm on the basis of desired agronomic traits. The method of the present invention is particularly adapted to moving genes or traits from one species into a second species.

The present invention further relates to two new and distinctive high yielding Pima Bt (*Bacillus thuringiensis*) Bollgard® cotton cultivars, designated 926 B Pima and 930 B Pima, which have been prepared in accordance with the method of the present invention. The present invention also relates to the seeds of these cotton cultivars, to the plants of these cotton cultivars and to methods for producing a cotton plant by crossing each of these cotton cultivars with itself or another cotton line.

DETAILED DESCRIPTION OF THE INVENTION

The present invention relates to a method for rapidly introducing genes into germplasm which involves the use of crossing, backcrossing, and intense selection for superior product quality and agronomic traits. More specifically, the method comprises the steps of: (a) crossing two parents of two different species, one of the parents (the donor parent) contains the gene of interest; (b) backcrossing the resultant progeny with the parent not containing the gene of interest (recurrent parent) for two to four backcrosses; © performing intense selection on a segregating generation of the progeny from the backcrossing step; and (d) selecting final germplasm on the basis of desired agronomic traits. The method of the present invention is particularly adapted to moving genes or traits from one species into a second species.

The present invention further relates to two new and distinctive high yielding Pima Bt (*Bacillus thuringiensis*) Bollgard® cotton cultivars, designated 926 B Pima and 930 B Pima, which have been prepared in accordance with the method of the present invention. The present invention also relates to the seeds of these cotton cultivars, to the plants of these cotton cultivars and to methods for producing a cotton plant by crossing each of these cotton cultivars with itself or another cotton line.

In the development of new varieties, especially involving interspecies crosses, in which backcrossing with a recurrent parent is the standard technique, it is conventional wisdom that a minimum of 6 and more preferably 7–10 backcrosses are necessary to introduce a gene from the donor parent into the recurrent parent. It has been discovered, in accordance with the present invention, that the number of backcrosses can be significantly reduced, e.g. to two to four backcrosses, by applying intense selection to the progeny of the final backcross (i.e., to the progeny of the second, third or fourth backcross), followed by selection for desired agronomic characteristics of the progeny of the intense selection. This discovery was totally unexpected and now enables the rapid production of new varieties using a backcrossing breeding technique.

Before the method of the present invention is described, the following definitions are provided to provide a clear and consistent understanding of the present invention.

DEFINITIONS

As used herein the term "American Pima" describes a sub-set of *Gossypium barbadense* cotton varieties developed in the desert southwest starting in the early 1900's. In 1908 the USDA moved it's *G. barbadense* breeding program to the Gila River Pima Indian reservation at Sacaton, Arizona.

Current American Pima cottons trace their background to a complex set of crosses involving the *G. barbadense* cottons Sea Island, Pima (an indirect selection from the Egyptian variety Mit Afifi), Tangus and the *G. hirsutum* variety Stoneville.

American Pima varieties are grown because of superior fiber qualities that command a monetary premium relative to *G. hirsutum* fiber that is long, strong, uniform and fme but mature. The fiber is used to spin very high quality yarns that contain cotton.

"$BC_n$" refers to the nth backcross with the recurrent parent. For example, the first backcross of the recurrent parent with the $F_1$ of the initial cross is $BC_1$; the second backcross of the progeny of the first backcross is $BC_2$, etc.

"$BC_nF_m$" refers to the mth generation of the nth backcross. For example, $BC_3F_1$ is the progeny (seeds) of the third backcross; $BC_3F_2$ is the progeny of plants grown from the seeds of $BC_3F_1$, etc. $BC_3F_1$ and $BC_3$ can be used interchangeably.

The term "Desired Agronomic Characteristics" refers to agronomic characteristics (which will vary from crop to crop and plant to plant) such as yield, maturity, pest resistance and lint percent which are desired in a commercially acceptable crop or plant. For example, improved agronomic characteristics for cotton include yield, maturity, fiber content and fiber qualities.

"Donor Parent" refers to the parent of a variety which contains the gene or trait of interest which is desired to be introduced into a second variety.

"ELS" is the abbreviation for "Extra Long Staple". ELS is the group classification for cottons in the longest staple length category. As used in practice and for commerce, ELS denotes varieties belonging to the species *G. barbadense* that have superior fiber qualities, including classification in the longest staple length category.

The term "Fiber Characteristics" refers to fiber strength, fiber length, micronaire, fiber elongation and uniformity of fiber.

The term "Fiber Elongation" also sometimes referred to as "E1" refers to the elongation of the fiber at the point of breakage in the strength determination.

The term "2.5% Fiber Span Length" refers to the longest 2.5% of a bundle of fibers expressed in inches as measured by a digital fibergraph.

The term "Fiber Strength" also sometimes referred to as "T1" refers to the force required to break a bundle of fibers. Fiber strength is expressed in millinewtons (mn) per tex on a stelometer.

"Fruiting Nodes" are the number of nodes on the main stem from which arise branches that bear fruit or boll in the first position.

The term "Gin Turnout" refers to fraction of lint in a machine harvested sample of seed cotton (lint, seed, and trash).

The term "Intense Selection" as used herein, refers to the degree of selection applied to the progeny of a backcross and means that the criteria for the selection is that (a) most or all of the traits or characteristics of the recurrent parent are selected for and (b) most or all of the traits or characteristics of the donor parent other than the gene of interest are selected against. If there are no progeny that meet the fill criteria after selecting for the recurrent parent traits, then the progeny that most closely fit the criteria are selected, followed by pedigree selection and a second generation of selection.

The term "Lint Yield" refer to the measure of the quantity of fiber produced on a given unit of land. Presented below in pounds of lint per acre.

"Lint Percent" refers to the lint (fiber) fraction of seed cotton (lint and seed).

The term "Maturity Rating" means a visual rating near harvest on the amount of open bolls on the plant. The rating range is from 1 to 5, 1 being early and 5 being late.

"Micronaire" refers to a measure of the fineness of the fiber. Within a cotton cultivar, micronaire is also a measure of maturity. Micronaire differences are governed by changes in perimeter or in cell wall thickness, or by changes in both. Within a variety, cotton perimeter is fairly consistent and maturity will cause a change in micronaire. Consequently, micronaire has a high correlation with maturity within a variety of cotton. Maturity is the degree of development of cell wall thickness. Micronaire may not have a good correlation with maturity between varieties of cotton having different fiber perimeter. Micronaire values range from about 2.0 to 6.0:

| Below 2.9 | Very fine | Possible. small perimeter but mature (good fiber), or large perimeter but immature (bad fiber). |
| --- | --- | --- |
| 2.9 to 3.7 | Fine | Various degrees of maturity and/or perimeter. |
| 3.8 to 4.2 | Average | Average degree of maturity and/or perimeter. |
| 4.3 & above | Coarse | Usually fully developed (mature), but larger perimeter. |

The term "Pima" is used in the same context as "American Pima". Note, the term "Peruvian Pima" is used to denote varieties developed in Peru from the American variety "Pima".

"Plant Height" refers to the average height in meters of a group of plants.

The term "Recurrent Parent" refers to the repeating parent (variety) in a backcross breeding program. The recurrent parent is the variety into which a gene or trait is desired to be introduced.

The term "Fiber Span Length" refers to the distance spanned by a specific percentage of fibers in a test specimen, where the initial starting point of the scanning in the test is considered 100 percent as measured by a digital fibergraph.

"Stringout Rating" also sometimes referred to as "Storm Resistance" refers to a visual rating prior to harvest of the relative looseness of the seed cotton held in the boll structure on the plant. The rating values are from 1 to 5 (tight to loose in the boll).

The term "Uniformity Ratio" refers to a measure of the relative fiber span length uniformity of a bundle of fibers. The uniformity ratio is determined by dividing the 50% fiber span length by the 2.5% fiber span length.

"Vegetative Nodes" are the number of nodes from the cotyledonary node to the first fruiting branch on the main stem of the plant.

In accordance with the present invention, a method is provided for rapidly introducing a gene or trait from one variety (a donor parent) into a second variety (a recurrent parent). The objectives of the present invention are twofold. The first objective is to move the transgene(s) to the recurrent parent phenotype. The second objective is to accomplish the first objective as quickly as genetically possible using minimal backcrossing generations in conjunction with intense selection. The method is particularly well adapted for introducing a gene or trait from one species (a donor parent) into a second species (a recurrent parent).

Generally, the present method comprises the steps of: (a) crossing a donor parent with a recurrent parent; (b) backcrossing the resulting progeny with the recurrent parent for two to four backcrosses; and (c) performing intense selection on a segregating generation of the progeny of the backcrossing step. In a preferred embodiment the method further comprises the step of: (d) selecting a final variety on the basis of desired agronomic characteristics. The donor parent contains the gene or trait of interest which can be any desired gene or trait. Intense selection is performed by selecting for traits and characteristics of the recurrent parent and selecting against any trait or characteristic of the donor parent. In a preferred embodiment, intense selection also includes selecting for fill expression of the gene or trait of interest.

More specifically, the method of the present invention comprises the steps of: (a) crossing said donor variety with said recurrent variety to produce a first familial generation variety; (b) crossing said recurrent variety with said first familial generation variety to produce a first backcross-first familial generation variety. In backcrosses involving genetically diverse recurrent and donor parents selection of $BC_1F_1$ plants which are most similar to the recurrent parent should be selected as the donor parent in the immediate subsequent backcross; (c) crossing said recurrent variety with said first backcross-first familial generation variety to produce a second backcross-first familial generation variety; and (d) subjecting a segregating generation of said second backcross-first familial generation variety to intense selection to produce a selected variety having the characteristics of said recurrent variety and the gene or trait of said donor variety. In a preferred embodiment the method further comprises the step of: (e) subjecting the selected variety to further selection for desired agronomic characteristics. In a preferred embodiment, the intense selection is performed on the second or third segregating generation of the progeny of step (c), i.e., $BC_2F_3$ or $BC_2F_4$.

In a second embodiment of the method of the present invention, an additional backcrossing step is incorporated between steps (c) and (d). According to this embodiment, the method further comprises the step of: (c1) crossing said recurrent variety with said second backcross-first familial generation variety to produce a third backcross-first familial generation variety. A segregating generation of said third backcross-first familial generation variety is subjected to the intense selection of step (d). In a preferred embodiment, the intense selection is performed on the second or third segregating generation of the progeny of step (c1), i.e., $BC_3F_3$ or $BC_3F_4$.

In a third embodiment of the method of the present invention, an additional backcrossing step is incorporated between steps (c1) and (d). According to this embodiment, the method further comprises the step of: (c2) crossing said recurrent variety with said third backcross-first familial generation variety to produce a fourth backcross-first familial generation variety. A segregating generation of said fourth backcross-first familial generation variety is subjected to the intense selection of step (d). In a preferred embodiment, the intense selection is performed on the second or third segregating generation of the progeny of step (c2), i.e., $BC_4F_3$ or $BC_4F_4$.

The present invention is further directed to novel varieties of Pima cotton which contain a Bollgard® gene. The *Bt* gene is the Bollgard® gene construct 531 which has been inserted into upland cotton. Specifically, the invention is directed to the novel cultivars designated 926 B Pima and 930 B Pima. The invention is further directed to methods of producing these cultivars as well as to methods of using the cultivars and plants and plant parts of the cultivars. Methods of using the cultivars include crossing a first parent cotton plant with a second parent cotton plant, wherein the first or second cotton plant is the cotton plant from the designated cultivars. Further, both first and second parent cotton plants may be from the same designated cultivar. Therefore, any methods using the cultivars of the present invention are part of this invention: selfing, backcrosses, hybrid breeding, and crosses to populations. Any plants produced using the present cultivars as a parent are within the scope of this invention. As used herein, the term "plant" includes plant cells, plant protoplasts, plant cells of tissue culture from which cotton plants can be regenerated, plant calli, plant clumps, and plant cells that are intact in plants or parts of plants, such as pollen, flowers, seeds, pods, leaves, stems, and the like. Thus, another aspect of this invention is to provide for cells which upon growth and differentiation produce the designated cultivars. Trolinder, N. L., et al., *Somatic embryogenesis and plant regeneration in cotton*, Plant Cell Reports 6:231–234 (1987); Bailey, C., et al., *Engineering 2,4-D resistance into cotton*, Theoretical and Applied Genetics 83:645–649 (1992).

The method of the present invention will be further illustrated with reference to cotton, and specifically with reference to *Gossypsium hirsutum* and *Gossypium barbadense*, and the *Bacillus thuringiensis* gene as the gene of interest. It is understood that the present method is equally applicable to any other agronomic or horticultural plant and to any other gene or trait of interest.

As previously discussed, the method involves a step of intense selection in which the traits of the recurrent parent, Pima (*G. barbadense*), in this example are selected for, and any trait of the donor parent, upland (*G. hirsutum*), in this example are selected against. The phenotypic differences between upland and Pima cotton are shown in Table 1.

TABLE 1

| | Phenotypic differences between Pima (*G. barbadense*) and Delta type Upland (*G. hirsutum*) cottons. | |
|---|---|---|
| Traits | Pima (*G. barbadense*) | Upland (*G. hirsutum*) |
| Leaves | Long leaf lobes ⅔-cut | Weak leaf lobes ½-cut or less |
| | Green | Olive |
| | Shiny | Less shiny |
| | One to five foliar nectaries on underside | One to three foliar nectaries on underside |
| | Leaf lobes slightly constricted at base | Leaf lobes not constricted at base |
| | Sinuses usually thrown up in folds | Sinuses not or only slightly overlapping |
| Stipules | 10–50 mm long | 4–15 mm long |
| Brateoles | Almost as broad as wide | Longer than broad |
| | Teeth 10–15 mm long | Teeth 7–12 mm long |
| Calyx | 6–10 mm long | 5–6 mm long |
| Petals | Up to 80 mm long | Up to, 50 mm long |
| | Yellow | Cream to pale yellow |
| | Dark red leaf spot at base | Leaf spot absent |
| Style | Exceeds androccium | More or less enclosed by androccium or somewhat exceeds androccium |
| Stamatal column | Long | Short |
| Stigma | Cleft near tip predominate in first flowers of the growing. season, thereafter occurs occasionally | United throughout |
| Pollen | Yellow | Cream to pale yellow (in specific upland used) |
| Capsules | Three celled | Four to five celled |
| | Prominently pitted | Slightly pitted |
| | Usually somewhat elongated | Broadly ovoid or subglobasose |
| Seed | Naked seed, seed fuzz absent or tutted ends | Thick coat of seed fuzz |
| Fiber properties (relative) | | |
| 2.5% span length | 25% longer than upland | 20% shorter than Pima. |
| Uniformity | 7% higher uniformity than Upland | 6% lower uniformity than Pima |
| Micronaire | 7% lower micronaire than Upland | 7% higher micronaire than Pima |
| Strength | 56% higher strength than Upland | 36% lower strength than Pima |

A cross is made between an agronomic Pima parent (recurrent parent) and an upland transgene(s) donor. The resulting $F_1$ seed is backcrossed to the recurrent parent. A larger number of crosses to the $F_1$ are made relative to conventional backcrossing. The amount of seed needed is increased because selection for the transgene(s) and the Pima parent will be exerted on the $BC_1$ plant population. A dominant transgene (i.e. Bt gene) segregates one to one for plants containing the Bt gene. Therefore, two times the number of plants needed to select for the Pima plant type are required. If two dominant transgenes are being transferred, four times the number of plants needed to select for the Pima plant type are required to recover both transgenes simultaneously.

The $BC_1$ seed (also referred to as ($BC_1F_1$ seed) is planted at a nursery where the plants ($BC_1F_1$) can be closely monitored, if desired. It is possible with the present invention to make the backcrosses without any selection. Segregation occurs as a result of the initial Pima by upland cross. All traits expressed represent homozygous loci donated by the Pima parent or heterozygous loci with an allele donated by both species used in the cross. Many identifiable heterozygous qualitatively inherited traits are observable. It is seen that variability between selected plants exists. In genetically narrow crosses this variability can be exploited by intercrossing. The objective is to proceed with a conventional breeding program within the population. As progeny homozygous for the transgene are identified and intercrossed, the need for extensive testing for the transgene (s) at every step is eliminated, providing the opportunity to concentrate on agronomic improvement. Alternatively, an initial selection for the transgene(s) can be exerted on the $BC_1$ plant population. Plants containing the transgene(s) of interest can then be used for further backcrossing. Although additional screening is not necessary at this stage for the operation of the present invention, progeny of plants with the most homozygous traits can be used in one embodiment for the $BC_2$ cross. Backcrossing to selected $BC_1F_1$'s reduces the number of undesirable G. hirsutum chromosomes far more effectively than random elimination expected through a backcross alone.

Again, a relatively large $BC_2F_1$ population from the $BC_2$ backcross is planted, selected for the transgene(s), if desired and self pollinated. A very large $BC_2F_2$ population from the selected $BC_2F_1$ population is planted, subjected to intense selection which can include selection for the transgene(s). In the present description for cotton, the traits of G. barbadense selected for and the traits of G. hirsutum selected against are shown in Table 2. The selected $BC_2F_2$ plants are then self pollinated.

TABLE 2

Traits for Selection

| Selected Against | Selected For |
|---|---|
| olive plant color | bright green plant color |
| reduced leaf lobe | deep leaf lobe |
| cream colored flower petal | full yellow colored flower petal |
| absent of no flower petal spot | petal spot presence |
| cream/intermediate pollen color | yellow pollen color |
| locule numbers other than three | three locule bolls |
| small gossypol glands | larger gossypol glands |
| shallow boll pitting | deep boll pitting |
| *inferior fiber quality (length < 1.30, strength < 32.5, mic > 4.0) | *pima fiber quality (length > 1.30, strength > 32.5, mic around 4.0) |
| <100% expression of the gene of interest from the donor parent | 100% expression of the gene of interest from the donor parent |

TABLE 2-continued

Traits for Selection

| Selected Against | Selected For |
|---|---|
| upland plant type | pima plant type |
| fuzzy seed (lint clings to seed coat) | naked seed (lint does not cling to seed coat) |

*fiber quality based on hand pulling and rating the fiber in the field.

$BC_2F_3$ seed from $BC_2F_2$ plant selections, possessing the transgene(s) are planted to row. Within selected rows plant selections are made for the recurrent parent plant type and desired agronomic characteristics, such as yield and fiber properties. Some breeders may choose to plant progeny rows and identify homozygous rows in season, i.e., herbicide resistance.

$BC_2F_4$ seed from $BC_2F_3$ plant selections homozygous for the transgene(s) are planted to row and selected for the recurrent parent plant type and desired agronomic characteristics, such as yield and fiber properties. Individual rows are bulk harvested and increased for replicated yield tests or plant selections can be made as in normal pedigree breeding.

The previous description related to the development of a Pima plant type containing the transgene(s) at the $BC_2F_4$ generation. In a similar manner, a Pima plant type containing a transgene of interest can be developed at the $BC_4F_4$ generation. As in the previous description, a cross is made between an agronomic Pima parent (recurrent parent) and an upland transgene donor. Conventional backcrossing is used through the $BC_2$. A large population of the progeny of the BC can be used without selection or selection can be based on the transgene.

The $BC_2$ seed is planted at a nursery where the plants can be closely monitored, if desired. For this example, selection for the transgene(s) is exerted on the $BC_2F_1$ plant population. The selected progeny is then backcrossed with either the recurrent parent, or it can be crossed with another superior Pima variety to direct the population genetics desired by the breeder.

A population breeding program can be initiated at this point to create variability within the backcross population. The object of increasing the variability is to develop a population that a number of Pima varieties with the transgene(s) of interest can be selected from over a number of years. It is also possible the transgene(s) will function more efficiently in certain Pima genetic backgrounds. If this is true, the probability of identifying those backgrounds will increase.

Seed from the $BC_3$ crosses are handled as the $BC_2$ population above. It may be possible to select desirable agronomic phenotypes resulting from increased variability in the Pima genetic background.

Seed from the $BC_4$ crosses are handled as the $BC_2$ population above. The recurrent genotypes or other genotypes used for breeding should consist of as wide an array as possible of superior Pima varieties to create variability.

Again, a relatively large $BC_4F_1$ population from the $BC_4$ backcross is planted, selected for the transgene(s), if desired and self pollinated. A very large $BC_4F_2$ population from the selected $BC_4F_1$ population is planted, subjected to intense selection which can include selection for the transgene(s). The traits for intense selection are set forth in Table 2. The selected $BC_4F_2$ plants are then self pollinated. Care should be taken not to narrow the Pima genetic base through severe selection for specific Pima phenotypes. Alternatively, the $BC_4F_2$ population is self-fertilized. The $BC_4F_3$ plants are then subjected to the intense selection.

$BC_4F_3$ seed from $BC_4F_2$ plant selections homozygous for the transgene(s) are planted to row. Within selected rows plant selections are made for the recurrent parent plant type and desired agronomic characteristics, such as yield and fiber properties. Alternatively, if intense selection is performed on the $BC_4F_3$ plants, the $BC_4F_4$ seed is used at this stage.

$BC_4F_4$ seed from $BC_4F_3$ plant selections (or $BC_4F_5$ seed from $BC_4 F_4$ plant selections in the alternative) homozygous for the transgene(s) are planted to row. Individual rows are bulk harvested and increased for replicated yield tests. If advantageous, individual plants can be selected for pedigree breeding.

In accordance with the method of the present invention, the Bollgard® gene (a $Bt$ gene) is moved from upland (*G. hirsutum*) to Pima S6 (*G. barbadense*) cotton. Utilizing upland cotton as the Bollgard® gene donor and Pima S6 as the recurrent parent exemplifies extensive genetic distance. Interspecific crosses approach the boundary of transfer of genetic material through sexual reproduction in higher plants. Conventionally, seven or more backcrosses is the minimum number of backcrosses accepted as needed to fully recover the Pima S6 recurrent parent phenotype. However, as shown in further detail herein, a Pima S6 recurrent parent phenotype having the Bollgard® gene is recovered with only three backcrosses.

Initially, the Bollgard® donor (e.g., Coker 312) is crossed with the recurrent Pima S6 parent. The $F_1$ is backcrossed with Pima S6. The progeny of the $BC_1$ backcross is again backcrossed with Pima S6, and the progeny of the $BC_2$ backcross is backcrossed with Pima S6. No selections are made in the course of the $BC_1$, $BC_2$ or $BC_3$ backcrosses. Progeny of the $BC_3$ backcross are self-pollinated for two generations to produce seed from the $BC_3F_2$ plants. The seed is planted and the $BC_3F_3$ plants are subjected to intense selection on the basis of the traits set forth in Table 2, including Pima fiber and Bollgard® gene expression. The plant rows are graded for yield and the best plants within the selected rows are harvested. Plant selections from $BC_3F_3$ are planted to row and the highest yielding, true breeding rows with Pima phenotype and homozygous for the Bollgard® gene are bulk harvested. $BC_3F_3$ derived lines are tested in two replicated tests, increased and bulk harvested without selection.

As discussed, selection is initiated in the $BC_3F_3$ generation (1995). Individual lines identified as homozygous for the Bollgard® gene are planted. Based on probabilities associated with backcrossing, genes from the Pima recurrent parent represented 93.75% of the genes in the population. The explosion of phenotypic variability caused by genes contributed by both species as they became homozygous is amazing. Because the $BC_3F_3$ population is segregating for a large number of phenotypic traits readily identifiable as belonging to *G. hirsutum* or *G. barbadense* tremendous selection pressure could be applied. The large number of segregating traits is the critical component that made the unanticipated success of recovering Pima S6 plant type with the Bollgard® gene possible. The full recovery of Pima S6 plant type is unexpected at backcross three.

For the intense selection, all plants that exhibited any trait derived from *G. hirsutum* was eliminated, with the exception of the Bollgard® gene. The backcross involved interspecific parents and an early backcross generation, recombination between chromosomes of the individual species were relatively infrequent. The species specific traits identified a segment of DNA possibly as large as entire chromosomes. Enormous quantities of genetic material belonging to *G. barbadense* is accumulated while eliminating *G. hirsutum* genetic material in the selected plants. The expressed *G. hirsutum* and *G. barbadense* traits facilitated precise and very effective selection for genes contributed by the recurrent parent, Pima S6. In contrast, conventional backcrossing is based on progressive but random accumulation of genetic material from the recurrent parent.

Rows are used to judge yield for two generations. Plant selections are considered exclusively in the highest yielding rows, homozygous for the Bollgard® gene. Yield is obviously important for commercial reasons. Yield also identifies lines containing genetic material that functions well together in the genome, regardless of species origin. Antagonistic gene interactions and problems at the chromosome level are common in interspecific crosses.

The suitability of the present invention is seen in comparing the $BC_3F_4$ plant selections with lines derived from additional backcrosses in accordance with conventional techniques. For this comparison, $BC_6F_3$ rows are planted in the same field as the $BC_3F_4$ plant selections. The $BC_6F_3$ rows expressed approximately 10% *G. hirsutum* traits than the $BC_3F_4$ rows. Fertility was reduced in the $BC_6F_3$ rows as evidenced by 2 to 4 seed per lock compared to 6 to 7 seed per lock in the $BC_3F_4$ rows. The $BC_6F_3$ material requires another backcross with selection to alleviate the fertility problems.

Plant selections from the $BC_3F_3$ planted the following year were free of readily identifiable traits introduced by the donor parent, with the exception of the Bollgard® gene. Plant and row selections were made exclusively on the quantitatively inherited traits yield, fiber properties and maturity. Four experimental strains derived from single plant selections from one $BC_3F_3$ row remain in testing. Two of the four remaining experimental strains are likely to be discarded because they are excessively late maturing. Based on plant selection, the selection index is 0.00056. Based on row selection, the selection index is 0.0041.

It is believed that three reasons contribute to the recovery of Pima S6 plant type with the Bollgard® gene where intense selection was initiated at the $BC_3F_3$ generation from an interspecific cross. First, massive quantities of identifiable, qualitative and quantitative, species specific genetic traits were generated as a result of interspecific genetic exchange. In many cases, intermediate expression of qualitative genes identified heterozygous plants. The traits were used to select for the *G. barbadense* parent and against the *G. hirsutum* parent. The haploid chromosome number in both species is 26. If no crossovers is assumed, and each chromosome is identified by one trait, 26 species specific traits are required to identify each chromosome and donor species. Crossovers did occur and one to many traits may have identified the same chromosome. The quantity of species specific traits is the primary reason for success.

Second, recombination was minimized. Recombination is reduced in interspecific exchanges. The chromosomes of the species involved are physically different, but are similar enough to pair. Initiation of selection in the $BC_3F_3$ reduced opportunities for recombination in higher backcross generations. Reduced recombination means on average, large species specific linkage groups were identified by the species specific genetic traits.

Third, extreme selection pressure was exerted on the $BC_3F_3$ plants and rows. Both qualitative and quantitative traits were used to identify Pima S6 plant type. All rows deficient in yield or fiber were eliminated. Within the selected rows only plants expressing traits inherited exclusively from the Pima S6 parent were selected. All selected plants were fiber tested for Pima fiber quality, all deficient plant selections were eliminated.

One very surprising development of this selection methodology is the superior fiber quality recovered in the initial selections. Fiber quality is critical in Pima cotton. All fiber traits are inherited quantitatively and very difficult to recover after interspecific crosses. The quick recovery of Pima fiber quality supports the hypothesis that significant quantities of upland genes were eliminated from the selected population by the $BC_3F_4$ generation when extreme selection pressure was applied to it.

The present invention is described by reference to the following Examples, which is offered by way of illustration and is not intended to limit the invention in any manner. The Examples describe the production of two novel Pima cotton varieties with the Bollgard® trait produced in accordance with the present invention.

EXAMPLE 1

Pima Cotton Cultivar 926 B Pima

Pima cotton cultivar 926 B Pima has superior characteristics and was developed in accordance with the method of the present invention from the cross of upland cotton Coker 312 (the donor parent) to Pima S6 (the recurrent parent). Pima S6 is a USDA released public variety. Backcrossing was used initially to transfer the $Bt$ gene into the new variety. The initial breeding was accomplished in greenhouses from the start of the project through $BC_3F_2$.

In the spring of 1995, seed from 241 individual $BC_3F_2$ plants developed at Scott, Miss. were sent to Casa Grande, Ariz. to be planted in the field for evaluation. Prior to planting, 10 seeds from each individual line were evaluated for $Bt$ expression in the seed. The object was to identify the lines homozygous for the $Bt$ gene. 65 $BC_3F_3$ tested 100% for the $Bt$ gene and were planted in the field in 1995 [for a selection pressure of 0.27 (65/241) or 27%]. Seed from each line was planted in as many rows as possible and thinned to one plant per foot to maximize the number of plants for selection.

Throughout the 1995 growing season plants exhibiting any upland cotton traits were tagged so they could be avoided at harvest. Examples of traits, against which selection was conducted, are light green plant color, reduced leaf lobe, cream flower petal color, absent or no flower petal spot, cream/intermediate pollen color, locule numbers different than three, small gossypol glands and shallow boll pitting.

In June, 1995 ten plants from each row were sampled for $Bt$ expression in plant tissue. It was observed that some plants exhibited weak expression. The reason for this is not known. It may be the testing technique or true weak expression of the gene in specific genotypes. Any row expressing less than 100% $Bt$ was discarded. Strong negative selection pressure was also placed on rows weakly expressing the $Bt$ gene [for a selection pressure of 0.149 (36/241) or 14.9%].

At harvest each row was visually graded for yield. Once the best lines were identified each plant in the selected line was examined by hand for fiber quality and naked seed (lint does not cling to the seed coat). Substandard plants were discarded [for a row selection pressure of 0.05 (12/241) or plant selection pressure of 0.033 or 3.3%].

Selected plants were ginned and the seed was examined for nakedness. Lines considered too fuzzy were discarded. The fiber of the remaining plants tested with standard instruments. All selections exhibiting substandard fiber were discarded. Twenty seeds from all selected lines were tested for $Bt$ expression. Twelve $BC_3F_4$ progeny were selected from four $BC_3F_4$ lines [for a selection pressure row of 0.017 (4/241) or 1.7% and a selection pressure plant of 0.003 (12/3600) or 0.03%].

The 12 $BC_3F_4$ selections were planted in single row plots replicated twice. Each plot was thinned to one plant per foot to facilitate single plant selection. Tissue from 20 plants per plot were tested for $Bt$ expression to confirm the $Bt$ gene was homozygous. As described above, selection was against all plants exhibiting any upland cotton traits.

At harvest, strong selection pressure was placed on yield. Only four lines appeared to have yield required for commercial release. Ten plant selections were made per selected line and the remainder of the four lines were harvested individually [for a 1996 selection pressure row of 0.333 (4/12) or 33.3%]. The bulked lines appeared very homogeneous. The ten selected plants in each line were fiber tested. The fiber quality averages were used to determine the quality of the bulked row selections.

In 1997, the four 1996 bulked lines were entered in two replicated tests, one in Casa Grande, Ariz. and the other in Maricopa, Ariz.; both are low elevation desert environments. The four 1996 bulked strains were increased on about 0.06 acres [for a final selection pressure plant of 0.00056 (2/3600) and row of 0.0041 (1/241)].

The $BC_3F_5$ plant selections were planted in single row plots replicated twice. Each plot was thinned to one plant per foot to facilitate single plant selection. Tissue from 20 plants per plot were tested for $Bt$ expression to confirm the plant selections $Bt$ gene was homozygous for the $Bt$ gene. Fourteen lines were bulk harvested for increase and replicated testing in 1998.

926 B Pima has superior lint yields to cultivars of similar maturity and adaptation type. It has good agronomic characteristics, including Pima fiber quality.

The criteria used to select in various generations include: lint yield, lint percent, fiber characteristics, maturity, storm resistance and insect resistance.

The cultivar has shown uniformity and stability to the traits, as described in the following variety description information. It has been advanced a sufficient number of generations with careful attention to uniformity of plant type. The line has been increased with continued observation for uniformity.

Cotton cultivar 926 B Pima has the following morphologic and other characteristics.

Variety Description Information

| | |
|---|---|
| Species: | *Gossypium barbadense* L. |
| Areas of Adaptation: | Western United States; Arizona, San Joaquin, New Mexico |
| General: | |
| Plant Habit | Spreading |
| Foliage | Intermediate |
| Stem Lodging | Intermediate |
| Fruiting Branch | Normal |
| Growth | Intermediate |
| Leaf Color | Dark green |
| Boll Shape | Length more than width |

-continued

| | |
|---|---|
| Boll Breadth Maturity: | Broadest at base |
| Date of 50% open bolls Plant: | Undetermined |
| 1st Fruiting Branch (from cotyledonary node) | Unknown |
| No. Nodes to 1st Fruiting Branch (Excluding cotyledonary node) | 8.75 |
| Mature Plant Height (from cotyledonary node to terminal) | 1.55 meters |
| Leaf(Upper most, fully expanded leaf): | |
| Type | Normal |
| Pubescence | Moderate |
| Nectaries | Present |
| Glands: | |
| Leaf | Present |
| Stem | Present |
| Calyx Lobe | Present |
| Flower: | |
| Petals | Yellow |
| Pollen | Yellow |
| Petal Spot | Present |
| Seed: | |
| Seed Index (g/100, fuzzy basis) | 11.6 |
| Boll: | |
| Lint Percent - Picked | 37.6 |
| Number of Seeds per Boll | 14.2 |
| Boll weight | 3.9 |
| Number of Locules per Boll | 3 |
| Boll Type | Open |
| Fiber Properties: | |
| Method | Standard Instrument |
| Length | 1.35 inches |
| Uniformity | 49.0% |
| Strength (T1) | 32.7 g/tex |
| Elongation (E1) | 8.0% |
| Micronaire | 3.9 |
| Diseases: | |
| Fusarium Wilt | Unknown |
| Verticillium Wilt | Good resistance |
| Nematodes, Insects and Pests: | |
| Root-Knot Nematode | Unknown |
| Boll Weevil | Unknown |
| Bollworm | Moderately resistant |
| Reniform Nematode | Unknown |
| Lygus | Moderately resistant |
| Pink Bollworm | Resistant |
| Tobacco Bud Worm | Resistant |

Deposit Information

A deposit of the cotton seed of 926 B Pima was made with the American Type Culture Collection, 10801 University Boulevard, Manassas, Va. 20110 on Jul. 15, 1998 and having ATCC Accession No. 203065.

The cultivar 926 B Pima is similar to Pima S6. While similar, there are numerous significant differences including: 926 B Pima has a higher seed cotton weight, higher yield, lower micronaire, longer fiber, lower fiber uniformity, lower fiber elongation, taller plant type and smaller seed than Pima S6. In addition to the yield of the present invention, is the presence of the *Bacillus thuringiensis* (*Bt*) construct 531 gene. No commercially available Pima variety carries the *Bt* gene. Results of pink bollworm damage are shown in Tables 3 and 4 and results of comparative head-to-head testing are shown in Table 5.

TABLE 3

Pink Bollworm Damage in Bt and Conventional Pima[1]
Percent of hard green bolls with pink bollworm exit holes

| Entry | Rep. 1 | Rep. 2 | Rep. 3 | Rep. 4 | Avg. |
|---|---|---|---|---|---|
| Pima S-7 | 6 | — | — | — | — |
| Pima S-6 | 16 | 10 | 30 | 10 | 16 |
| 926 B Pima | 0 | 0 | 0 | 0 | 0 |

[1]Sampled 50 hard green bolls per plot. Inspected each boll for exit holes. Cracked only those bolls with exit holes to verify pink bollworm damage. Maricopa, Arizona on August 12, 1997.

TABLE 4

Pink Bollworm Damage in Bt and Conventional Pima[1]
Percent of hard green bolls with pink bollworm exit holes

| Entry | Rep. 1 | Rep. 2 | Rep. 3 | Rep. 4 | Avg. |
|---|---|---|---|---|---|
| Pima S-6 | 12 | 20 | 36 | 16 | 21 |
| 926 B Pima | 0 | 0 | 0 | 0 | 0 |
| PS6531-328-6B | 0 | 0 | 0 | 0 | 0 |
| 930 B Pima | 0 | 0 | 0 | 0 | 0 |
| PS6531-332-6B | 0 | 0 | 0 | 0 | 0 |

[1]Sampled 25 bolls per plot. Hard green, unopened bolls from the top portion of the plants were chosen. Inspected each boll for larvae and/or exit holes. Maricopa, Arizona on September 16, 1997

TABLE 5

1997 Head to Head Comparison

| Name | Seed Cotton | Lint % | Lint Yield | Mic | Len | Ur | T1 | E1 | Plt Hgt | Mat Rtg | Seed Index |
|---|---|---|---|---|---|---|---|---|---|---|---|
| Casa Grande, Arizona - 7CGMC138 | | | | | | | | | | | |
| 926 B Pima. | 4190 | 37.7 | 1578 | 3.6 | 1.34 | 49.8 | 31.4 | 8.2 | 5.0 | 4.5 | 11.2 |
| Conquistador | 4126 | 36.0 | 1483 | 3.9 | 1.34 | 50.3 | 33.1 | 8.3 | 2.8 | 3.0 | 12.2 |
| Pima S-7 | 3970 | 36.5 | 1447 | 3.9 | 1.34 | 50.5 | 32.6 | 7.9 | 2.8 | 3.0 | 12.4 |
| Pima S-6 | 3519 | 37.7 | 1325 | 3.9 | 1.29 | 50.3 | 31.6 | 8.7 | 3.5 | 4.5 | 13.0 |
| Average | 3928 | 37.2 | 1459 | 3.8 | 1.32 | 49.8 | 32.3 | 8.3 | 4.0 | 4.1 | 12.0 |
| LSD (.05) | 131 | 0.4 | 82 | 0.1 | ns | ns | ns | ns | 0.8 | 0.2 | 0.5 |
| Cv (%) | 3.9 | 0.7 | 3.8 | 1.9 | 2.5 | 1.7 | 2.4 | 4.6 | 12.8 | 10.9 | 3.1 |

TABLE 5-continued

1997 Head to Head Comparison

| Name | Seed Cotton | Lint % | Lint Yield | Mic | Len | Ur | T1 | E1 | Plt Hgt | Mat Rtg | Seed Index |
|---|---|---|---|---|---|---|---|---|---|---|---|
| Reps | 4 | 4 | 4 | 4 | 4 | 4 | 4 | 4 | 4 | 4 | 4 |
| | | | | Maricopa, Arizona | | | | | | | |
| 926 B Pima | 3854 | 37.6 | 1448 | 4.1 | 1.36 | 48.3 | 34.1 | 7.7 | 4.1 | 4.3 | 12.0 |
| Conquistador | 3621 | 37.3 | 1351 | 4.1 | 1.30 | 48.4 | 34.6 | 8.0 | 3.1 | 2.8 | 11.7 |
| Pima S-7 | 3535 | 38.2 | 1349 | 4.1 | 1.33 | 49.3 | 36.2 | 7.2 | 2.8 | 2.3 | 11.7 |
| Pima S-6 | 3157 | 38.4 | 1212 | 4.1 | 1.32 | 49.4 | 33.8 | 8.1 | 3.8 | 4.0 | 12.8 |
| Average | 3542 | 37.9 | 1340 | 4.1 | 1.32 | 48.8 | 34.7 | 7.7 | 3.4 | 3.3 | 12.0 |
| LSD (.05) | 211 | 0.5 | 80 | ns | 2.62 | 0.7 | 1.1 | 0.3 | 0.7 | 0.8 | 0.6 |
| CV (%) | 3.9 | 0.8 | 3.9 | 2.3 | 1.3 | 1.0 | 2.1 | 3.0 | 11.7 | 13.6 | 3.4 |
| Reps | 4 | 4 | 4 | 4 | 4 | 4 | 4 | 4 | 4 | 4 | 4 |
| | | | | Two Location Summary | | | | | | | |
| 926 B Pima | 4022 | 37.6 | 1513 | 3.9 | 1.35 | 49.0 | 327 | 8.0 | 4.6 | 4.4 | 11.6 |
| Conquistador | 3874 | 36.6 | 1417 | 4.0 | 1.32 | 49.3 | 33.9 | 8.1 | 2.9 | 2.9 | 12.0 |
| Pima S-7 | 3754 | 37.3 | 1399 | 4.0 | 1.33 | 50.0 | 34.3 | 7.5 | 2.7 | 2.8 | 12.0 |
| Pima S-6 | 3338 | 38.0 | 1268 | 4.0 | 1.30 | 49.8 | 32.7 | 8.4 | 3.7 | 4.3 | 12.9 |
| Average | 3747 | 37.4 | 1399 | 4.0 | 1.32 | 49.5 | 33.4 | 8.0 | 3.4 | 3.6 | 12.1 |
| LSD (.05) | 180 | 0.5 | 66 | 0.1 | 0.03 | 0.7 | 0.8 | 0.3 | 0.5 | 0.5 | 0.5 |
| CV (%) | 4.7 | 1.4 | 4.7 | 2.4 | 2.1 | 1.4 | 2.5 | 3.8 | 12.9 | 12.5 | 3.9 |
| Reps | 8 | 8 | 8 | 8 | 8 | 8 | 8 | 8 | 8 | 8 | 8 |

Seed Cotton - Seed cotton pounds/acre
Lint % - Lint percent
Lint Yield - Lint yield pounds/acre
MIC - Micronaire
Len - 2.5% Span length (inches)
UR - Uniformity ratio percent
T1 - Fiber strength (gr/tex)
E1 - Fiber elongation
Ph - Plant height rating (1 = short, 5 = very tall)
Mat Rtg - Maturity rating
Seed Index - Seed Index (g/100)

EXAMPLE 2

Cotton Cultivar 930 B Pima

In the spring of 1995, seed from 241 individual $BC_3F_2$ plants developed at Scott, Miss. were sent to Casa Grande, Ariz. to be planted in the field for evaluation. Prior to planting, 10 seeds from each individual line were evaluated for *Bt* expression in the seed. The object was to identify the lines homozygous for the *Bt* gene. 65 $BC_3F_3$ tested 100% for the *Bt* gene and were planted in the field in 1995. Seed from each line was planted in as many rows as possible and thinned to one plant per foot to maximize the number of plants for selection.

Throughout the 1995 growing season plants exhibiting any upland cotton traits were tagged so they could be avoided at harvest. Examples of traits selected against are light green plant color, reduced leaf lobe, cream petal color, absent or no petal spot, cream/intermediate pollen color, locule numbers different than three, small gossypol glands, ovate shaped bolls and shallow boll pitting.

In June, 1995 ten plants from each row were sampled for *Bt* expression in plant tissue. It was observed that some plants exhibited weak expression. The reason is not known, it may be technique or true weak expression of the gene in specific genotypes. Any row expressing less than 100% *Bt* was discarded. Strong negative selection pressure was also placed on rows weakly expressing the *Bt* gene.

At harvest each row was visually graded for yield. Once the best lines were identified each plant in the selected line was examined by hand for fiber quality and naked seed. Substandard plants were discarded.

Selected plants were ginned and the seed was examined for nakedness, lines considered too fuzzy were discarded. The fiber of the remaining plants was tested with standard instruments. All selections exhibiting substandard fiber were discarded. 20 seeds from all selected lines were tested for Bt expression. Twelve lines were advanced to the $BC_3F_4$ generation.

The 12 $BC_3F_4$ selections were planted in single row plots replicated twice. Each plot was thinned to one plant per foot to facilitate single plant selection. Tissue from 20 plants per plot were tested for *Bt* expression to confirm the *Bt* gene was homozygous. As described above, all plants exhibiting any upland cotton traits were selected against.

At harvest, strong selection pressure was placed on yield. Only four lines appeared to have yield required for commercial release. Ten plant selections were made per selected line and the remainder of the four lines were harvested individually. The bulked lines appeared very homogeneous. The ten selected plants in each line were fiber tested with standard instruments. The fiber quality averages were used to determine the quality of the bulked row selections.

In 1997, the four 1996 bulked lines were entered in two replicated tests, one in Casa Grande, Ariz. and the other in Maricopa, Ariz.; both are low elevation desert environments. The four 1996 bulked strains were increased on about 0.06 acres.

The $BC_3F_5$ plant selections were planted in single row plots replicated twice. Each plot was thinned to one plant per foot to facilitate single plant selection. Tissue from 20 plants per plot were tested for *Bt* expression to confirm the *Bt* gene was homozygous. Fourteen lines were bulk harvested for increase and replicated testing in 1998.

930 B Pima has superior lint yields to cultivars of similar maturity and adaptation type. It has good agronomic characteristics, including Pima fiber quality.

The criteria used to select in various generations include: lint yield, lint turnout, fiber characteristics, maturity, storm resistance, disease tolerance, early season vigor.

The cultivar has shown uniformity and stability to the traits, as described in the following variety description information. It has been advanced a sufficient number of generations with careful attention to uniformity of plant type. The line has been increased with continued observation for uniformity.

Cotton cultivar 930 B Pima has the following morphologic and other characteristics.

Variety Description Information

| | |
|---|---|
| Species: | *Gossypium barbadense* L. |
| Areas of Adaptation: | Western United States, Arizona, San Joaquin, New Mexico |
| General: | |
| Plant Habit | Spreading |
| Foliage | Intermediate |
| Stem Lodging | Intermediate |
| Fruiting Branch | Normal |
| Growth | Intermediate |
| Leaf Color | Dark green |
| Boll Shape | Length more than width |
| Boll Breadth | Broadest at middle |
| Maturity: | |
| Date of 50% open bolls | Undetermined |
| Plant: | |
| 1st Fruiting Branch (from cotyledonary node) | Unknown |
| No. Nodes to 1st Fruiting Branch (Excluding cotyledonary node) | 9 |
| Mature Plant Height (from cotyledonary node to terminal) | 1.5 meters |
| Leaf(Upper most, fully expanded leaf): | |
| Type | Normal |
| Pubescence | Moderate |
| Nectaries | Present |
| Glands: | |
| Leaf | Present |
| Stem | Present |
| Calyx Lobe | Present |
| Flower: | |
| Petals | Yellow |
| Pollen | Yellow |
| Petal Spot | Present |
| Seed: | |
| Seed Index(g/100, fuzzy basis) | 11.7 |
| Boll: | |
| Lint Percent - Picked | 38.9 |
| Number of Seeds per Boll | 14.9 |
| Grams Seed Cotton per Boll | 4 |
| Number of Locules per Boll | 3 |
| Boll Type | Open |
| Fiber Properties: | |
| Method | Standard Instrument |
| Length | 1.32 inches |
| Uniformity | 48.4% |
| Strength (T1) | 33.2 g/tex |
| Elongation (E1) | 8.2% |
| Micronaire | 3.9 |
| Diseases: | |
| Fusarium Wilt | Unknown |
| Verticillium Wilt | Good resistant |
| Nematodes, Insects and Pests: | |
| Root-Knot Nematode | Unknown |
| Boll Weevil | Unknown |
| Bollworm | Moderately Resistant |
| Reniform Nematode | Unknown |
| Lygus | Moderately Resistant (compared to Upland cotton) |
| Pink Bollworm | Resistant |
| Tobacco Bud Worm | Resistant |

Deposit Information

A deposit of the cotton seed of 930 B Pima was made with the American Type Culture Collection, 10801 University Boulevard, Manassas, Va. 20110 on Jul. 15, 1998 and having ATCC Accession No. 203066.

The cultivar 930 B Pima is similar to Pima S6. While similar, there are numerous differences including: 930 B Pima has higher seed cotton weight, higher yield, lower micronaire, longer fiber, lower fiber uniformity, lower fiber elongation, taller plant type and smaller seed than Pima S6. In addition to the yield of the instant invention, is the presence of the *Bacillus thuringiensis* (*Bt*) construct 531 gene. No commercially available Pima variety carries the *Bt* gene. Results of pink bollworm damage are shown in Tables 6 and 7 and results of comparative head-to-head testing are shown in Table 8.

TABLE 6

Pink Bollworm Damage in Bt and Conventional Pima[1]
Percent of hard green bolls with pink bollworm exit holes

| Entry | Rep. 1 | Rep. 2 | Rep. 3 | Rep. 4 | Avg. |
|---|---|---|---|---|---|
| Pima S-7 | 6 | — | — | — | — |
| Pima S-6 | 16 | 10 | 30 | 10 | 16 |
| 930 B Pima | 0 | 0 | 0 | 0 | 0 |

[1]Sampled 50 hard green bolls per plot. Inspected each boll for exit holes. Cracked only those bolls with exit holes to verify pink bollworm damage. Maricopa, Arizona on August 12, 1997.

TABLE 7

Pink Bollworm Damage in Bt and Conventional Pima[1]
Percent of hard green bolls with pink bollworm exit holes

| Entry | Rep. 1 | Rep. 2 | Rep. 3 | Rep. 4 | Avg. |
|---|---|---|---|---|---|
| Pima S-6 | 12 | 20 | 36 | 16 | 21 |
| 926 B Pima | 0 | 0 | 0 | 0 | 0 |
| PS6531-328-6B | 0 | 0 | 0 | 0 | 0 |
| 930 B Pima | 0 | 0 | 0 | 0 | 0 |
| PS6531-332-6B | 0 | 0 | 0 | 0 | 0 |

[1]Sampled 25 bolls per plot. Hard green, unopened bolls from the top portion of the plants were chosen. Inspected each boll for larvae and/or exit holes. Maricopa, Arizona on September 16, 1997.

TABLE 8

1997 Head to Head Comparison

| Name | Seed Cotton | Lint % | Lint Yield | Mic | Len | Ur | T1 | E1 | Plt Hgt | Mat Rtg | Seed Index |
|---|---|---|---|---|---|---|---|---|---|---|---|
| Casa Grande, Arizona - 7CG5313 | | | | | | | | | | | |
| 930 B Pima | 3956 | 38.0 | 1502 | 3.8 | 1.32 | 48.8 | 32.8 | 8.5 | 3.8 | 3.8 | 11.9 |
| Conquistador | 4126 | 36.0 | 1483 | 3.9 | 1.34 | 50.3 | 33.1 | 8.3 | 2.8 | 3.0 | 12.2 |
| Pima S-7 | 3970 | 36.5 | 1447 | 3.9 | 1.34 | 50.5 | 32.6 | 7.9 | 2.8 | 3.0 | 12.4 |
| Pima S-6 | 3519 | 37.7 | 1325 | 3.9 | 1.29 | 50.3 | 31.6 | 8.7 | 3.5 | 4.5 | 13.0 |
| Average | 3928 | 37.2 | 1459 | 3.8 | 1.32 | 49.8 | 32.3 | 8.3 | 4.0 | 4.1 | 12.0 |
| LSD (.05) | 131 | 0.4 | 82 | 0.1 | ns | ns | ns | ns | 0.8 | 0.2 | 0.5 |
| Cv (%) | 3.9 | 0.7 | 3.8 | 1.9 | 2.5 | 1.7 | 2.4 | 4.6 | 12.8 | 10.9 | 3.1 |
| Reps | 4 | 4 | 4 | 4 | 4 | 4 | 4 | 4 | 4 | 4 | 4 |
| Markopa, Arizona | | | | | | | | | | | |
| 930 B Pima | 3953 | 38.9 | 1539 | 4.1 | 1.33 | 48.1 | 33.7 | 7.9 | 3.8 | 4.3 | 11.5 |
| Conquistador | 3621 | 37.3 | 1351 | 4.1 | 1.30 | 48.4 | 34.6 | 8.0 | 3.1 | 2.8 | 11.7 |
| Pima S-7 | 3535 | 38.2 | 1349 | 4.1 | 1.33 | 49.3 | 36.2 | 7.2 | 2.8 | 2.3 | 11.7 |
| Pima S-6 | 3157 | 38.4 | 1212 | 4.1 | 1.32 | 49.4 | 33.8 | 8.1 | 3.8 | 4.0 | 12.8 |
| Average | 3566 | 38.2 | 1362 | 4.1 | 1.32 | 48.8 | 34.6 | 7.8 | 3.4 | 3.3 | 11.9 |
| LSD (.05) | 211 | 0.5 | 80 | ns | 2.62 | 0.7 | 1.1 | 0.3 | 10.7 | 0.8 | 10.6 |
| CV (%) | 3.9 | 0.8 | 3.9 | 2.3 | 1.3 | 1.0 | 2.1 | 3.0 | 11.7 | 13.6 | 3.4 |
| Reps | 4 | 4 | 4 | 4 | 4 | 4 | 4 | 4 | 4 | 4 | 4 |
| Two Location Summary | | | | | | | | | | | |
| 930 B Pima | 3.954 | 38.5 | 1520 | 3.9 | 1.32 | 48.4 | 33.2 | 8.2 | 3.8 | 4.0 | 11.7 |
| Conquistador | 3874 | 36.6 | 1417 | 4.0 | 1.32 | 49.3 | 33.9 | 8.1 | 2.9 | 2.9 | 12.0 |
| Pima S-7 | 3754 | 37.3 | 1399 | 4.0 | 1.33 | 50.0 | 34.3 | 7.5 | 2.7 | 2.8 | 12.0 |
| Pima S-6 | 3338 | 38.0 | 1268 | 4.0 | 1.30 | 49.8 | 32.7 | 8.4 | 3.7 | 4.3 | 12.9 |
| Average | 3730 | 37.6 | 1401 | 4.0 | 1.32 | 49.4 | 33.5 | 8.0 | 3.3 | 3.5 | 12.1 |
| LSD (.05) | 180 | 0.5 | 66 | 0.1 | 0.03 | 0.7 | 0.8 | 0.3 | 0.5 | 0.5 | 0.5 |
| CV (%) | 4.7 | 1.4 | 4.7 | 2.4 | 2.1 | 1.4 | 2.5 | 3.8 | 12.9 | 12.5 | 3.9 |
| Reps | 8 | 8 | 8 | 8 | 8 | 8 | 8 | 8 | 8 | 8 | 8 |

Seed Cotton - Seed cotton pounds/acre
Lint % - Lint percent
Lint Yield - Lint yield pounds/acre
MIC - Micronaire
Len - 2.5% Span length (inches)
UR - Uniformity ratio percent
T1 - Fiber strength (gr/tex)
E1 - Fiber elongation
Ph - Plant height rating (1 = short, 5 = very tall)
Mat Rtg - Maturity rating
Seed Index - Seed Index (g/100)

Although the foregoing invention has been described in some detail by way of illustration and example for purposes of clarity and understanding, it will be obvious that certain changes and modifications may be practiced within the scope of the invention, as limited only by the scope of the appended claims.

BIBLIOGRAPHY

Allard, R. W., *Principles of Plant Breeding*, John Wiley & Sons, New York, London (1960)

Fehr, W. R., *Principles of Cultivar Development*, Vol. 2 Macmillan Publishing Co., New York, N.Y., (1987)

Mayo, O., *The Theory of Plant Breeding*, 2nd Ed., Clarendon Press, Oxford, (1987)

Welsh, J. R, *Fundamentals of Plant Genetics and Plant Breeding*, John Wiley & Sons, New York, N.Y., (1981)

What is claimed is:

1. A cotton cultivar seed designated 926 B Pima having ATCC Accession No. 203065.

2. A plant or its parts produced by growing the seed of claim 1.

3. Pollen of the plant of claim 2.

4. An ovule of the plant of claim 2.

5. A cotton plant having the physiological and morphological characteristics of the plant of claim 2.

6. Tissue culture of the plant of claim 2.

7. A cotton plant regenerated from the tissue culture of claim 6, wherein said cotton plant is capable of expressing all the physiological and morphologic characteristics of cotton cultivar 926B.

8. A method for producing a cotton cultivar seed comprising crossing a first cultivar parent cotton plant with a second cultivar parent cotton plant and harvesting the resultant cultivar cotton seed, wherein said first or second parent cotton plant is the cotton plant of claim 2.

9. A hybrid seed produced by the method of claim 8.

10. A hybrid plant or its parts produced by growing said hybrid cotton seed of claim 9.

11. Seed produced from said hybrid plant of claim 10.

12. A method for producing a hybrid cotton seed comprising crossing a plant according to claim 2 with another, different cotton plant.

13. A hybrid seed produced by the method of claim 12.

14. A hybrid plant or its parts produced by growing said hybrid cotton seed of claim 13.

15. Seed produced from said hybrid plant of claim 14.

* * * * *